(12) United States Patent
Corl (10) Patent No.: US 11,998,389 B2
(45) Date of Patent: Jun. 4, 2024

(54) FOCUSED ROTATIONAL IVUS TRANSDUCER USING SINGLE CRYSTAL COMPOSITE MATERIAL

(71) Applicant: PHILIPS IMAGE GUIDED THERAPY CORPORATION, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 417 days.

(21) Appl. No.: 17/498,793

(22) Filed: Oct. 12, 2021

(65) Prior Publication Data

US 2022/0022845 A1    Jan. 27, 2022

Related U.S. Application Data

(63) Continuation of application No. 14/137,465, filed on Dec. 20, 2013, now Pat. No. 11,141,134, which is a
(Continued)

(51) Int. Cl.
*A61B 8/00* (2006.01)
*A61B 6/46* (2024.01)
(Continued)

(52) U.S. Cl.
CPC ............ *A61B 8/4483* (2013.01); *A61B 6/461* (2013.01); *A61B 8/0891* (2013.01); *A61B 8/12* (2013.01);
(Continued)

(58) Field of Classification Search
CPC ......... A61B 6/461; A61B 8/0891; A61B 8/12; A61B 8/14; A61B 8/445; A61B 8/4483;
(Continued)

(56) References Cited

U.S. PATENT DOCUMENTS

| 4,692,654 A | 9/1987 | Umemura |
| 5,164,920 A | 11/1992 | Bast |
| (Continued) |

FOREIGN PATENT DOCUMENTS

| JP | S61146098 | 7/1986 |
| JP | 62261300 A | 11/1987 |
| (Continued) |

OTHER PUBLICATIONS

International Search Report and Written Opinion of PCT/US2013/077140, dated May 26, 2014.
(Continued)

*Primary Examiner* — Michael T Rozanski (57) ABSTRACT

An ultrasound transducer for use in intravascular ultrasound (IVUS) imaging systems including a single crystal composite (SCC) layer is provided. The transducer has a front electrode on a side of the SCC layer; and a back electrode on the opposite side of the SCC layer. The SCC layer may have a bowl shape including pillars made of a single crystal piezoelectric material embedded in a polymer matrix. Also provided is an ultrasound transducer as above, with the back electrode split into two electrodes electrically isolated from one another. A method of forming an ultrasound transducer as above is also provided. An IVUS imaging system is provided, including an ultrasound emitter and receiver rotationally disposed within an elongate member; an actuator; and a control system controlling emission of pulses and receiving ultrasound echo data associated with the pulses. The ultrasound emitter and receiver include an ultrasound transducer as above.

12 Claims, 9 Drawing Sheets

Related U.S. Application Data continuation-in-part of application No. 14/135,063, filed on Dec. 19, 2013, now Pat. No. 9,345,450.

(60) Provisional application No. 61/745,425, filed on Dec. 21, 2012.

(51) Int. Cl.
| | |
|---|---|
| *A61B 8/08* | (2006.01) |
| *A61B 8/12* | (2006.01) |
| *A61B 8/14* | (2006.01) |
| *B06B 1/06* | (2006.01) |
| *H10N 30/092* | (2023.01) |
| *H10N 30/85* | (2023.01) |

(52) U.S. Cl.
CPC ............... *A61B 8/14* (2013.01); *A61B 8/445* (2013.01); *B06B 1/0622* (2013.01); *B06B 1/067* (2013.01); *H10N 30/092* (2023.02); *H10N 30/852* (2023.02); *B06B 2201/76* (2013.01); *Y10T 29/49005* (2015.01)

(58) Field of Classification Search
CPC ... B06B 1/0622; B06B 1/067; B06B 2201/76; H10N 30/092; H10N 30/852; Y10T 29/49005
See application file for complete search history.

(56) References Cited

U.S. PATENT DOCUMENTS

| | | | |
|---|---|---|---|
| 5,368,035 | A | 11/1994 | Hamm |
| 5,474,071 | A | 12/1995 | Chapelon |
| 5,792,058 | A | 8/1998 | Lee |
| 6,371,915 | B1 | 4/2002 | Koger |
| 6,390,985 | B1 | 5/2002 | Mamayek |
| 6,566,265 | B2 | 5/2003 | Esashi |
| 6,709,396 | B2 | 3/2004 | Flesch |
| 7,514,851 | B2 | 4/2009 | Wilser |
| 2001/0031922 | A1 | 10/2001 | Weng |
| 2004/0015084 | A1 | 1/2004 | Flesch |
| 2005/0085730 | A1 | 4/2005 | Flesch |
| 2006/0100522 | A1 | 5/2006 | Yuan |
| 2006/0276711 | A1 | 12/2006 | Yuan |
| 2007/0016065 | A1 | 1/2007 | Hastings |
| 2007/0100239 | A1 | 5/2007 | Nair |
| 2010/0076318 | A1 | 3/2010 | Rehrig |
| 2010/0160788 | A1 | 6/2010 | Davies |
| 2010/0168582 | A1 | 7/2010 | Yuan |
| 2010/0240998 | A1 | 9/2010 | Calisti |
| 2013/0088118 | A1 | 4/2013 | Ho |
| 2013/0303907 | A1 | 11/2013 | Corl |
| 2014/0187964 | A1 | 7/2014 | Corl |

FOREIGN PATENT DOCUMENTS

| | | |
|---|---|---|
| JP | 63114500 A | 5/1988 |
| JP | 64018399 A | 1/1989 |
| JP | 2000139916 A | 5/2000 |
| WO | 199833430 A1 | 8/1998 |
| WO | 2011033272 A1 | 3/2011 |

OTHER PUBLICATIONS

Akiho, M. et al "Revised Handbook of Ultrasonic Diagnostic Equipments", Electronic Inductires Associate of Japan, Jan. 20, 1997.

International Searching Authority/European Patent Office, "Communication—The Supplementary European Search Report", for EP Application No. 13866074.1, dated Jul. 18, 2016.

Hackenberger, W. et al "Broad Band Single Crystal Transducer ofr Contrast Agent Harmonic Imaging", 2003 IEEE Ultrasonics Symposium, Oct. 2003, vol. 1.

Yuan, J. et al "60 Mhz PMN-PT based 1-3 Composite Transducer for IVUS Imaging", 2008 IEEE International Ultrasonics Symposium, Nov. 2008.

International Searching Authority/European Patent Office, "Communication—The Supplementary European Search Report", for EP Application No. 13864028.9, dated Jul. 13, 2016.

International Search Report and Written Opinion of PCT/US2013/07575, dated Apr. 10, 2014.

Sun, Ping et al "High Frequency PMN-PT 1-3 Composite Transducer for Ultrasonic Imaging Application", Ferroelectronics, vol. 408, No. 1, 2010.

Fig. 9 ial applications, each which is hereby incorporated by reference in its entirety.

FOCUSED ROTATIONAL IVUS TRANSDUCER USING SINGLE CRYSTAL COMPOSITE MATERIAL

CROSS-REFERENCE TO RELATED APPLICATIONS

The present application is a continuation of U.S. patent application Ser. No. 14/137,465, filed Dec. 20, 2013, now U.S. Pat. No. 11,141,134, which is a continuation-in-part of U.S. patent application Ser. No. 14/135,063, filed Dec. 19, 2013, now U.S. Pat. No. 9,345,450, which claims priority to and the benefit of U.S. Provisional Patent Application No. 61/745,425, filed Dec. 21, 2012, each which is hereby incorporated by reference in its entirety.

TECHNICAL FIELD

The present disclosure relates generally to intravascular ultrasound (IVUS) imaging inside the living body and, in particular, to an IVUS imaging catheter that relies on a mechanically-scanned ultrasound transducer, including embodiments where the transducer includes a single crystal composite material.

BACKGROUND

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. The ultrasound waves pass easily through most tissues and blood, but they are partially reflected from discontinuities arising from tissue structures (such as the various layers of the vessel wall), red blood cells, and other features of interest. The IVUS imaging system, which is connected to the IVUS catheter by way of a patient interface module (PIM), processes the received ultrasound echoes to produce a cross-sectional image of the vessel where the catheter is placed.

In a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the catheter. A fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of these pulse/acquisition cycles occurring during a single revolution of the transducer.

In the typical rotational IVUS catheter, the ultrasound transducer is a lead-zirconate-titanate (PZT) piezoelectric ceramic element with low electrical impedance capable of directly driving an electrical cable connecting the transducer to the imaging system hardware. In this case, a single pair of electrical leads (or coaxial cable) can be used to carry the transmit pulse from the system to the transducer and to carry the received echo signals from the transducer back to the imaging system by way of a patient interface module ("PIM") where the echo signals can be assembled into an image. Since the catheter driveshaft and transducer are spinning (in order to scan a cross-section of the artery) and the imaging system hardware is stationary, there must be an electromechanical interface where the electrical signal traverses the rotating junction. In rotational IVUS imaging systems, this need can be satisfied by rotary transformers, slip rings, rotary capacitors, etc.

While existing IVUS catheters deliver useful diagnostic information, there is a need for enhanced image quality to provide improved assessment of the vessel condition. For improved image quality compared to that provided by conventional rotational IVUS, it is desirable to use a transducer with broader bandwidth and to incorporate focusing into the transducer. One approach to form a focused ultrasound beam is to incorporate an acoustic lens mounted on a conventional PZT transducer. For example, a silicone rubber lens with an acoustic velocity of 1.0 mm/μsec is widely used for elevation focus in phased-array ultrasound systems. While the acoustic lens may improve the lateral and elevation focus of a conventional PZT transducer used in a rotational IVUS system, the lens fabrication on such a small scale is complex, and the lens may introduce artifacts in the resulting image. Furthermore, the lens does not solve the problem of relatively narrow bandwidth of the conventional PZT transducer which limits the range resolution.

Another possibility for improvement is the piezoelectric micro-machined ultrasound transducer (PMUT) fabricated using a polymer piezoelectric material, potentially providing greater than 100% bandwidth for optimum resolution in the range (radial) direction, and a spherically-focused aperture for optimum azimuthal and elevation resolution. While this polymer PMUT technology offers improved resolution in all three dimensions, it requires active electronics (including an amplifier) immediately adjacent to the transducer and within the flexible driveshaft, significantly increasing the complexity of the device. Furthermore, the transmit efficiency of polymer piezoelectric material is much lower than that of the traditional lead-zirconate-titanate (PZT) piezoelectric ceramic; therefore, the signal-to-noise ratio of a PMUT device will be compromised unless the deficiency in acoustic output can be compensated for by improved transmit electronics and/or other signal processing advances.

Accordingly, there remains a need for improved devices, systems, and methods for implementing a focused ultrasound transducer, providing wide bandwidth and high efficiency for use in a rotational intravascular ultrasound imaging system.

SUMMARY

According to some embodiments, an ultrasound transducer for use in intra-vascular ultrasound (IVUS) imaging systems is provided that includes a single crystal composite (SCC) layer; a front electrode on a side of the SCC layer; and a back electrode on the opposite side of the SCC layer. In some embodiments, the SCC layer includes pillars made of a single crystal piezoelectric material. The pillars are embedded in a polymer matrix in some instances. The SCC layer has a dish shape, defined by a concave surface and opposing convex surface, in some embodiments. The back electrode is split into two electrodes electrically decoupled from one another in some implementations.

A method of forming an ultrasound transducer for use in IVUS imaging systems in some embodiments includes etching a single crystal; forming a polymer layer on the etched single crystal to form a single crystal composite (SCC) having a first thickness; placing a first electrode on a first side of the SCC; forming the SCC to a second thickness; placing a second electrode on a second side of the SCC; and placing the SCC on a molded tip.

An IVUS imaging system according to some embodiments may include an ultrasound emitter and receiver rotationally disposed within an elongate member; an actuator coupled to the ultrasound emitter, the actuator moving the ultrasound emitter through at least a portion of an arc; and a control system controlling the emission of a sequence of pulses from the ultrasound emitter and receiving from the receiver ultrasound echo signals associated with the pulses, the control system processing the ultrasound echo signals to generate a cross-sectional image of the vessel. In some embodiments the ultrasound emitter and receiver comprises an ultrasound transducer including a single crystal composite (SCC) layer; a front electrode; and a back electrode. In some embodiments the SCC layer includes pillars made of a single crystal piezoelectric material. The pillars are embedded in a polymer matrix in some instances. The SCC layer has a dish shape, with opposing concave and convex surfaces, in some embodiments.

These and other embodiments of the present disclosure will be described in further detail below with reference to the following drawings.

BRIEF DESCRIPTION OF THE DRAWINGS

In the figures, elements having the same reference number have the same or similar functions and/or features.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Embodiments disclosed herein are for an apparatus and a method of fabrication of the apparatus, the apparatus including a focused transducer to be used in a rotational IVUS catheter. A transducer as disclosed herein provides a broad bandwidth ultrasound signal having focused beam propagation. Such a transducer provides high resolution in all three dimensions (range, lateral and elevation) in an intravascular ultrasound imaging application. In some embodiments, an IVUS catheter of the present disclosure provides a wide bandwidth, focused ultrasound beam without the need for an amplifier or other active electronics mounted in close proximity to the transducer within the rotating flexible driveshaft. An ultrasound transducer according to embodiments disclosed herein may include a single crystal composite material that provides a wide bandwidth, focused beam. The single crystal composite material is shaped into an element having a curvature designed to provide a focused beam (e.g., defining a concave emitting surface for the ultrasound transducer) in some instances.

Figure 1:
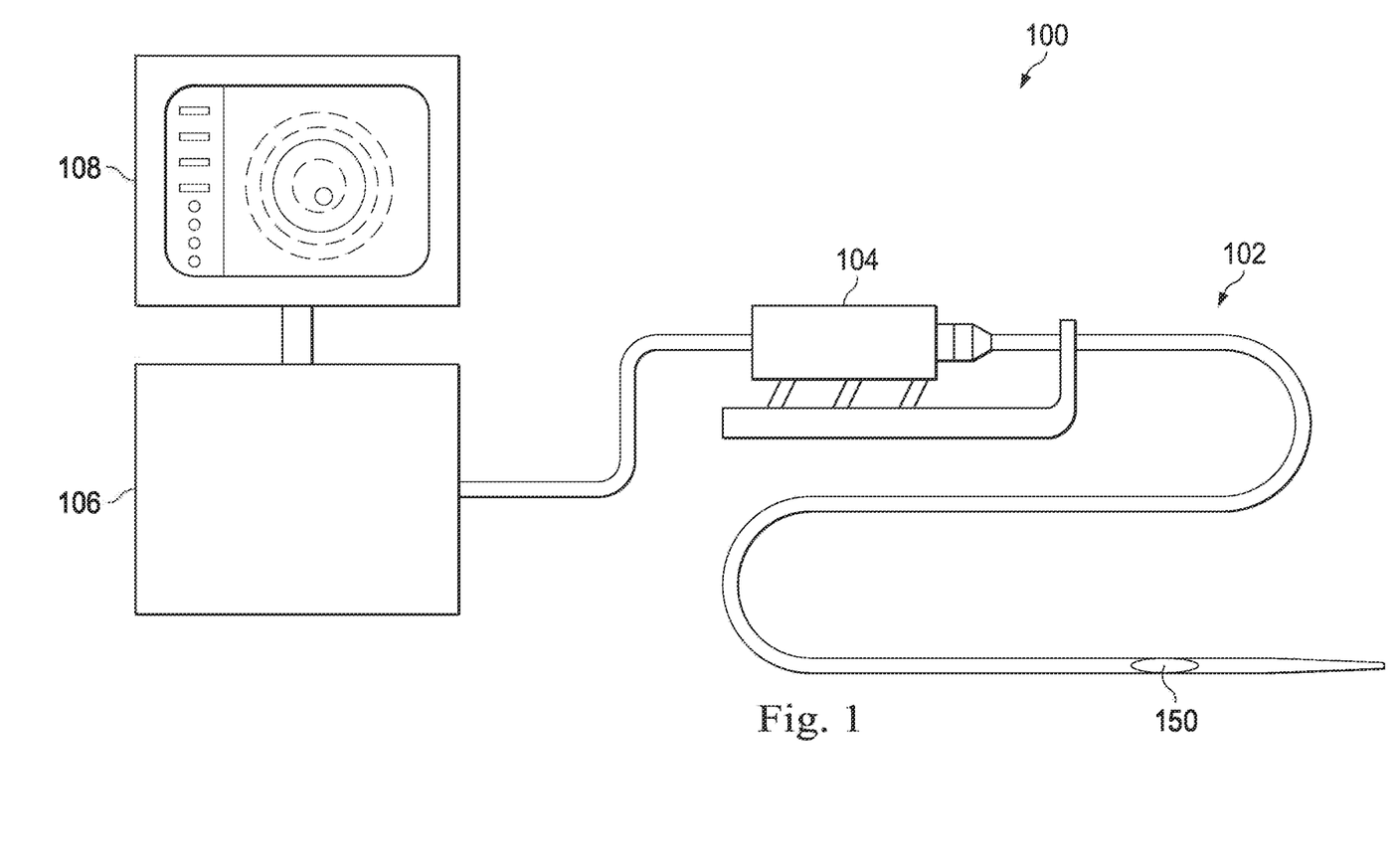
FIG. 1 is a schematic view of an imaging system according to an embodiment of the present disclosure.

FIG. 1 shows an IVUS imaging system 100 according to an embodiment of the present disclosure. In some embodiments of the present disclosure, the IVUS imaging system 100 is a rotational IVUS imaging system. In that regard, the main components of the rotational IVUS imaging system are a rotational IVUS catheter 102, a patient interface module (PIM) 104, an IVUS console or processing system 106, and a monitor 108 to display the IVUS images generated by the IVUS console 106. Catheter 102 includes an ultrasound transducer 150 in some embodiments. PIM 104 implements the appropriate interface specifications to support catheter 102. According to some embodiments, PIM 104 generates a sequence of transmit trigger signals and control waveforms to regulate the operation of ultrasound transducer 150.

Ultrasound transducer 150 transmits ultrasound signals substantially perpendicular to the longitudinal axis of the catheter into the vessel lumen and outward towards the vessel wall. The ultrasound emission from the transducer is activated by a corresponding electrical signal received from PIM 104. Ultrasound transducer 150 also converts ultrasound echo signals from the vessel tissue (and other reflectors) into electrical signals that are communicated to PIM 104.

Figure 2:
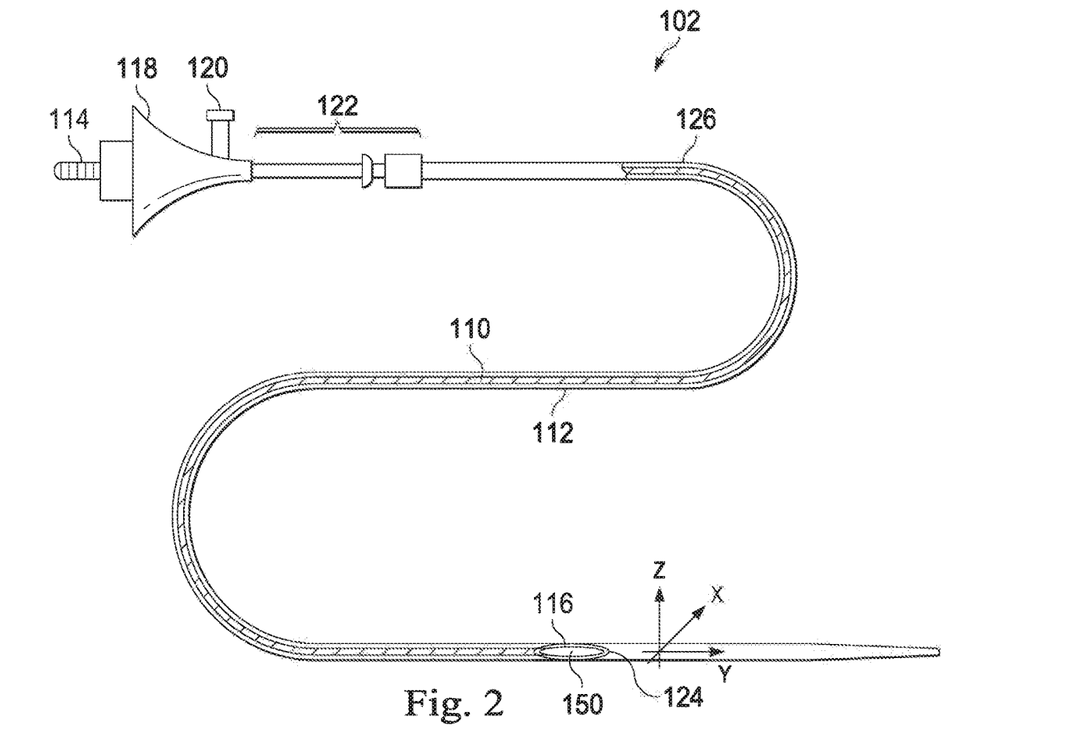
FIG. 2 is a diagrammatic, partial cutaway perspective view of an imaging device according to an embodiment of the present disclosure.

FIG. 2 shows a diagrammatic, partial cutaway perspective view of catheter 102, according to an embodiment of the present disclosure. FIG. 2 shows additional detail regarding rotational IVUS catheter 102. Rotational catheter 102 includes an imaging core 110 and an outer catheter/sheath assembly. Imaging core 110 includes a flexible drive shaft that is terminated at the proximal end by a rotational interface 114 providing electrical and mechanical coupling to PIM 104 (cf. FIG. 1). The distal end of the flexible drive shaft of the imaging core 110 is coupled to a transducer housing 116 containing ultrasound transducer 150.

Catheter/sheath assembly 112 includes a hub 118 supporting rotational interface 114 and provides a bearing surface and a fluid seal between rotating and non-rotating elements of catheter 102. In some embodiments, hub 118 includes a luer lock flush port 120 through which saline is injected to flush out the air and fill the inner lumen of the sheath with an ultrasound-compatible fluid at the time of use of the catheter. Saline or other similar fluid is required, since ultrasound frequencies are highly attenuated by air, and strongly reflected at any air-solid or air-liquid interface. Saline also provides a biocompatible lubricant for the rotating driveshaft. In some implementations, hub 118 is coupled to a telescope 122 that includes nested tubular elements and a sliding fluid seal that permits catheter/sheath assembly 112 to be lengthened or shortened. Telescope 122 facilitates axial movement of the transducer housing within an acoustically transparent window 124 at the distal portion of catheter/sheath assembly 112.

In some embodiments, window 124 is composed of thin-walled plastic tubing fabricated from material(s) that readily conduct ultrasound waves between the transducer and the vessel tissue with minimal attenuation, reflection, or refraction. A proximal shaft 126 of catheter/sheath assembly 112 bridges the segment between telescope 122 and window 124. In some embodiments, proximal shaft 126 is composed of a material or composite that provides a lubricious internal lumen and optimum stiffness to catheter 102. In some embodiments, the catheter/sheath assembly 112 and/or the window 124 includes features as described in U.S. Provisional Patent Application No. 61/746,958, titled "INTRAVASCULAR ULTRASOUND CATHETER FOR MINIMIZING IMAGE DISTORTION, filed Dec. 28, 2012, which is hereby incorporated by reference in its entirety.

Figure 3:
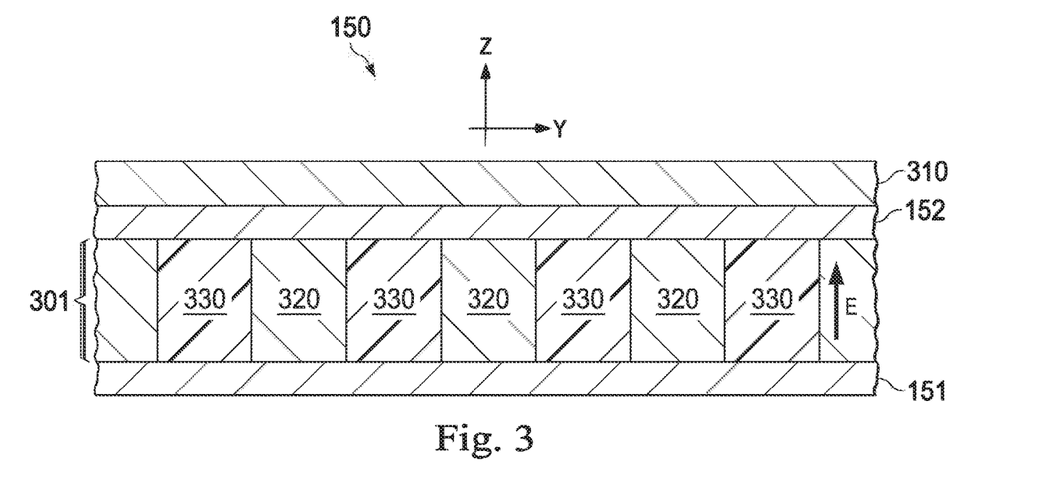
FIG. 3 shows a partial view of an ultrasound transducer according to an embodiment of the present disclosure.

FIG. 3 shows a partial cross-sectional view of ultrasound transducer 150 according to some embodiments disclosed herein. Transducer 150 includes a single crystal composite material (SCC) 301 having pillars 320 of a single crystal piezoelectric material embedded in a polymer matrix 330. The illustrated composite is commonly referred to as 1-3 composite, indicative of the one-dimensional connectivity of the piezoelectric material (continuous in the Z-direction, but not in the X- or Y-direction) and the three-dimensional connectivity of the polymer matrix (continuous in the X-, Y-, and Z-directions). In some embodiments, the single crystal piezoelectric material forming pillars 320 is lead magnesium niobate-lead titanate (PMN-PT). In some embodiments polymer matrix 330 is formed by epoxy or other polymer material. The epoxy or other material used as filler in polymer matrix 330 provides flexibility to the SCC forming ultrasound transducer 150. Depending on the particular requirements of the application in terms of flexibility, strength, and acoustic properties, suitable filler materials may include a more rigid epoxy such as EPO-TEK 301, a flexible epoxy such as one of the Mereco 1650 series formulations, a silicone such as polydimethylsiloxane (PDMS), another polymer such as metallocene-catalyzed poly-dicyclopentadiene, or a syntactic foam fabricated from one of the aforementioned polymers loaded with microballoons.

The polymer matrix 330 reduces the acoustic impedance of the SCC 301 compared to that of PMN-PT single crystal material or PZT ceramic. The improved acoustic impedance match between the SCC and the surrounding medium (saline) promotes high efficiency coupling and broad bandwidth for transducer 150. The piezoelectric crystal material is chosen for its high electromechanical coupling coefficient, further improving the transducer efficiency. Furthermore, the composite structure of the SCC 301 supports a "pillar-mode" of vibration which is more efficient than the "plate mode" of vibration found in traditional transducers fabricated from bulk piezoelectric material (either single crystal or ceramic).

In some embodiments, an impedance matching layer 310 is included with ultrasound transducer 150. In some embodiments, matching layer 310 may be a quarter-wave matching layer added to SCC 301 to enhance the acoustic coupling from the transducer into the surrounding medium to improve the transducer efficiency and increase its bandwidth. In other embodiments, the acoustic matching of the SCC 301 to the medium is close enough that an added matching layer is not needed.

According to some embodiments disclosed herein, pillars 320 form structures elongated in an axial direction (Z-axis in FIG. 3) having a narrow width in cross section (Y-axis in FIG. 3 or X-axis not shown). Preferably, the aspect ratio of width to height for a pillar should be 0.6 or less to ensure that the efficient pillar mode of vibration predominates. To achieve a 40 MHz center frequency of operation typical for IVUS imaging, the thickness of SCC 301 might be approximately 30 μm, and in that case, the lateral dimension of a single pillar is preferably 18 μm or less.

In some embodiments SCC 301 is deformed into a curved shape to produce a focused transducer. For example, SCC 301 may be deformed into a spherical curvature to form a concave bowl-shaped structure with a center of curvature at the desired focal distance, such as 1.5 mm from the front surface of the transducer. For a typical IVUS transducer having a diameter of 0.50 mm, the preferred focal length would be in the range from 1 mm to 2 mm. In some embodiments, the curvature may be designed to correct for cylindrical aberration caused by the cylindrical catheter/sheath 102. In this case, the curvature in the YZ-plane might be circular, but with a different radius of curvature from the radius of curvature in the XZ-plane.

In some embodiments SCC 301 promises high efficiency and broad bandwidth for ultrasound generation and sensing, which is desirable for IVUS imaging applications. Piezoelectric materials used for single crystal composite may have a high electromechanical coupling coefficient. For example, some formulations of PMN-PT exhibit k33=0.90, versus k-33=0.72 for a PZT-5H composition commonly used for traditional IVUS transducers. Note that k33 is the pillar-mode electromechanical coupling coefficient. A single crystal composite fabricated from PMN-PT having k33=0.90, may yield a kt value of 0.855 for the composite. Note that kt is the plate-mode electromechanical coupling coefficient, and for comparison, the corresponding kt value for bulk PZT-5H commonly used for IVUS transducers is approximately 0.5. Since one-way energy conversion efficiency is proportional to kt2, the round trip energy efficiency is proportional to the fourth power of the kt ratio, and the expected improvement due to an increase in kt from 0.5 up to 0.855 would be almost 10 dB. For reference, see Ren, Kailiang; Yiming Liu; Xuecang Geng; Hofmann, H. F.; Zhang, Q. M., "Single crystal PMN-PT/Epoxy 1-3 composite for energy-harvesting application," Ultrasonics, Ferroelectrics and Frequency Control, IEEE Transactions on, vol. 53, no. 3, pp. 631,638, March 2006, which is hereby incorporated by reference in its entirety.

In some embodiments of SCC 301, undesirable lateral vibration modes (in the XY-plane of FIG. 3) are suppressed, particularly those close in frequency to the desired ultrasound operating frequency. The lateral resonance frequency for a narrow pillar 320 having a width-to-height aspect ratio of 0.6 or less is substantially higher than the fundamental frequency of the desired pillar-mode resonance, and any lateral vibrations that are excited may be dampened by absorption in the relatively soft polymer matrix 330 that surrounds the pillars 320. In addition, the cross-sectional profile of the pillar may be altered from the simple rectangle or square cross-section typically used for single crystal composite materials, thereby reducing or eliminating lateral resonance modes. Furthermore, the periodicity of the pillar matrix may be varied or randomized across the pillar array to reduce coherence with respect to lateral vibrations, thereby suppressing low frequency lateral modes that might otherwise arise from array periodicity.

As described above, a high electromechanical coupling coefficient may be obtained using single crystal composite material, and the lateral modes may be suppressed, resulting in efficient transformation of electrical energy delivered into the pillar mode of vibration in pillars 320, and into the corresponding thickness-mode vibration (Z-axis in FIG. 3) of SCC 301. Further as described above, polymer matrix 330 reduces the acoustic impedance of SCC 301 compared to that of solid single crystal material. For example, in some embodiments SCC 301 may include between 20% and 80% by volume of polymer matrix 330. Such a composite may exhibit an acoustic impedance as low as 5 MRayls (for the lowest percentage of piezoelectric material) or as high as 20 MRayls (for the highest percentage of piezoelectric material). For comparison, the acoustic impedance of PZT ceramic is approximately 34 MRayls and that of PMN-PT is typically 25 MRayls. The low acoustic impedance of a single crystal composite material is better matched to tissue acoustic impedance (~1.5 MRayls), therefore promoting high efficiency and broad bandwidth for single crystal composite ultrasound transducer 150.

The dimensions of SCC 301 vary according to the specific application sought. For example, the target ultrasound frequency and bandwidth determine the specific dimensions of SCC 301 in some instances. In some embodiments pillars 320 are about 20 µm in lateral dimension (XY plane in FIG. 3) with 10 µm kerf widths. The thickness of the SCC substrate might be approximately 30 µm for the typical 40 MHz center frequency of a transducer intended for IVUS imaging. For high frequency IVUS, it may be desirable to have even smaller pillars and kerfs in SCC 301. In some embodiments, single crystal materials may be desirable in SCC 301 for high frequency applications because single crystals may be more easily patterned using deep reactive ion etching (DRIE). DRIE techniques may be used to pattern the crystalline substrate with micron accuracy to fabricate SCC 301 materials on a wafer scale.

The volume fraction of piezoelectric 320 in SCC 301 may also vary according to the application. For example, the volume fraction of piezoelectric 320 affects the piezoelectric performance of the transducer (in terms of efficiency and bandwidth), the acoustic matching to the medium (which affects overall system efficiency and bandwidth), and the flexibility of the substrate (which affects the ability to deflect the substrate into a spherical shape to produce a focused transducer). Typical values for volume fraction of piezoelectric in single crystal composite range from 20% to 80%. A volume fraction of approximately 50% is commonly chosen as a good compromise in terms of performance, flexibility, and manufacturability.

Figure 4:
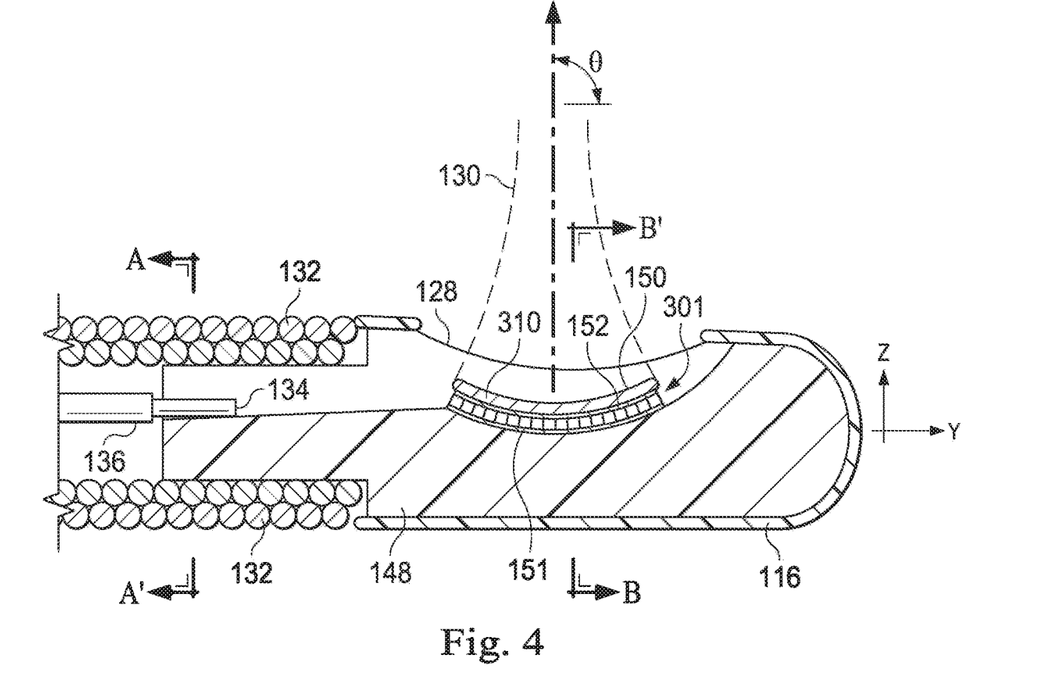
FIG. 4 shows a partial cross-sectional side view of a distal portion of an imaging device acco

FIG. 4 shows a partial perspective view of transducer housing 116, including ultrasound transducer 150 according to some embodiments. Ultrasound transducer 150 includes SCC 301 and impedance matching layer 310. Other details of ultrasound transducer 150 are omitted in FIG. 4, for clarity. It is understood that ultrasound transducer 150 in FIG. 4 may include the same or similar elements as shown in FIG. 3. For example, ultrasound transducer 150 in FIG. 4 may include back electrode 151, and front electrode 152.

Transducer housing 116 is in a distal portion of catheter 102 according to an embodiment of the present disclosure. In particular, FIG. 4 shows an expanded view of aspects of the distal portion of imaging core 110. In this exemplary embodiment, imaging core 110 is terminated at its distal tip by housing 116. Housing 116 may be fabricated from stainless steel or other suitable biocompatible material, and have a bullet-shaped or rounded nose, and an aperture 128 for an ultrasound beam. Thus, ultrasound beam 130 may emerge from housing 116, through aperture 128. In some embodiments, flexible driveshaft 132 of imaging core 110 is composed of two or more layers of counter wound stainless steel wires. Flexible driveshaft 132 is welded or otherwise secured to housing 116 such that rotation of flexible driveshaft 132 imparts rotation to housing 116. In the illustrated embodiment, an electrical cable 134 with an optional shield 136 provides electrical power to SCC 301. Electrical cable 134 extends through an inner lumen of flexible driveshaft 132 to the proximal end of imaging core 110 where it is terminated to the electrical connector portion of the rotational interface 114 (cf. FIG. 2). SCC 301 is mounted onto molded backing 148. Molded backing 148 may be formed of a polymer material such as epoxy, and serve as an acoustic backing material to absorb ultrasound reverberations propagating within housing 116. Molded backing 148 provides strain relief for electrical cable 134 at the point of soldering to electrodes 151 and 152 in some instances.

According to some embodiments, molded backing 148 is formed with a concave upper surface such that when ultrasound transducer 150 is placed on the concave upper surface and adhered in place, the flexibility of SCC 301 allows ultrasound transducer 150 to conform to the curvature of the backing 148 and retain a corresponding curved shape. The convex shape of the ultrasound transducer 150 may have a center of curvature along the axis of the ultrasound beam direction BD. FIG. 4 shows a beam direction BD substantially perpendicular to the longitudinal axis of catheter 102. One of ordinary skill will recognize that the angle between the beam direction and the longitudinal axis of the catheter may have values less than or greater than 90°, depending on the desired features of the catheter. In that regard, in some implementations, the ultrasound transducer 150 is mounted such that the ultrasound beam 130 propagates at an oblique angle with respect to the longitudinal axis of the catheter. Such an oblique angle for the ultrasound beam direction BD may be advantageous for reducing ultrasound reverberations from the catheter window 124, or for facilitating Doppler ColorFlo imaging as described in U.S. patent application Ser. No. 13/892,108, titled "Device and System for Imaging and Blood Flow Velocity Measurement" and filed May 10, 2013, which is hereby incorporated by reference in its entirety.

The curvature adopted by ultrasound transducer 150 according to embodiments as disclosed herein provides focusing for beam 130. In some embodiments transducer may be approximately 500 µm in diameter with a focal length (radius of curvature) of approximately 1.5 mm, corresponding to an f:3 relative aperture. This f:3 relative aperture provides a reasonable depth of field for IVUS imaging, and places the geometric focus of ultrasound beam 130 approximately 1 mm outside the typical catheter window 124, having a 1 mm diameter. For a spherically-focused transducer, the depth of the bowl-shaped curvature can be approximated as transducer diameter, divided by eight times the f:number, or approximately 20 µm for the illustrative example provided here.

In some embodiments an acoustic lens may be used to provide focusing to beam 130. To produce an acoustic lens, some embodiments may use silicone or other polymer exhibiting low acoustic velocity relative to that of the surrounding medium (saline). Silicone materials suitable for forming an acoustic lens are available with acoustic velocities in the range of 1.0 mm/µsec, compared to an acoustic velocity in saline or blood of approximately 1.5 mm/µsec. A spherically-curved acoustic lens formed from such a low-velocity silicone material, and having a center thickness of approximately 60 µm may provide a similar f:3 focusing power to the curved transducer described above having a 20 µm deep bowl-shaped curvature. A spherically-curved lens may be formed by applying a controlled volume of liquid to the surface of a circular transducer, and allowing surface tension to draw the liquid into a spherical shape before the liquid cures to form a solid/rubbery lens. Alternatively, a spherical lens can be formed by molding the silicone material to the desired shape. One potential disadvantage of the lens-based focusing versus the curved transducer approach is that the lens may give rise to reflections, reverberation, attenuation, and other artifacts that may degrade the image quality.

Figure 5A:
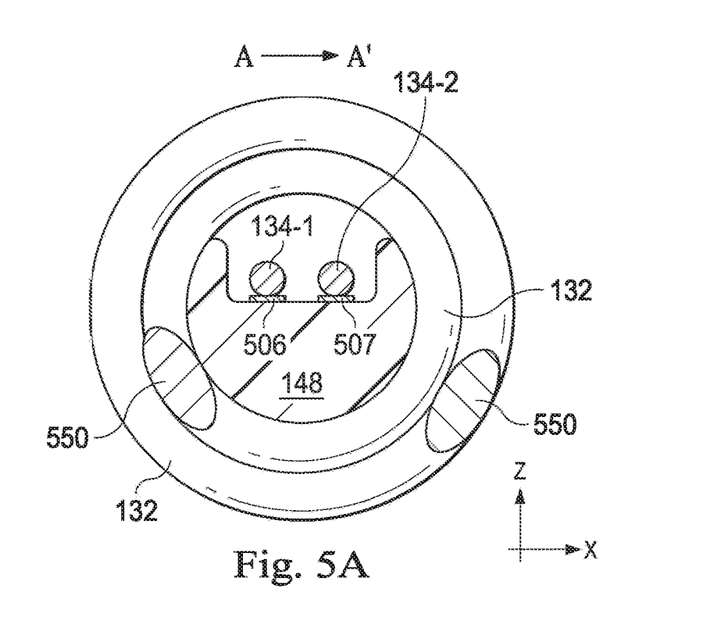
FIG. 5A shows a partial cross-sectional axial view of the distal portion of the imaging device of FIG. 4 along section line A-A'.

FIG. 5A shows a partial cross-section view of a transducer housing including electrical leads 134-1 and 134-2, according to some embodiments. FIG. 5A results from taking a cut away view of FIG. 4 along line AA'. Electrical leads 134-1 and 134-2 may be collectively referred to as leads 134 (cf. FIG. 4). Leads 134 may be coupled to bonding pad 506 (lead 134-1) and to bonding pad 507 (lead 134-2). Bonding pads 506 and 507 may have electrical contact with either of electrodes 151 and 152 in ultrasound transducer 150. In some instances, electric leads 134-1 and 134-2 provide opposite polarities of an electrical excitation signal coupled to SCC 301 through electrodes 151 and 152. In some embodiments lead 134-1 is coupled to back electrode 151 and lead 134-2 is coupled to front electrode 152. Further, according to some embodiments leads 134-1 and 134-2 are coupled to separate portions of back electrode 151, electrically isolated from one another. In such configurations, front electrode 152 may be a floating electrode having no direct electrical connection to any external potential, in which case it may assume a potential midway between the voltages provided by leads 134-1 and 134-2 to the isolated segments of back electrode 151. Embodiments having a floating electrode 152 may simplify the electrical connections used inside housing 116.

Figure 5B:
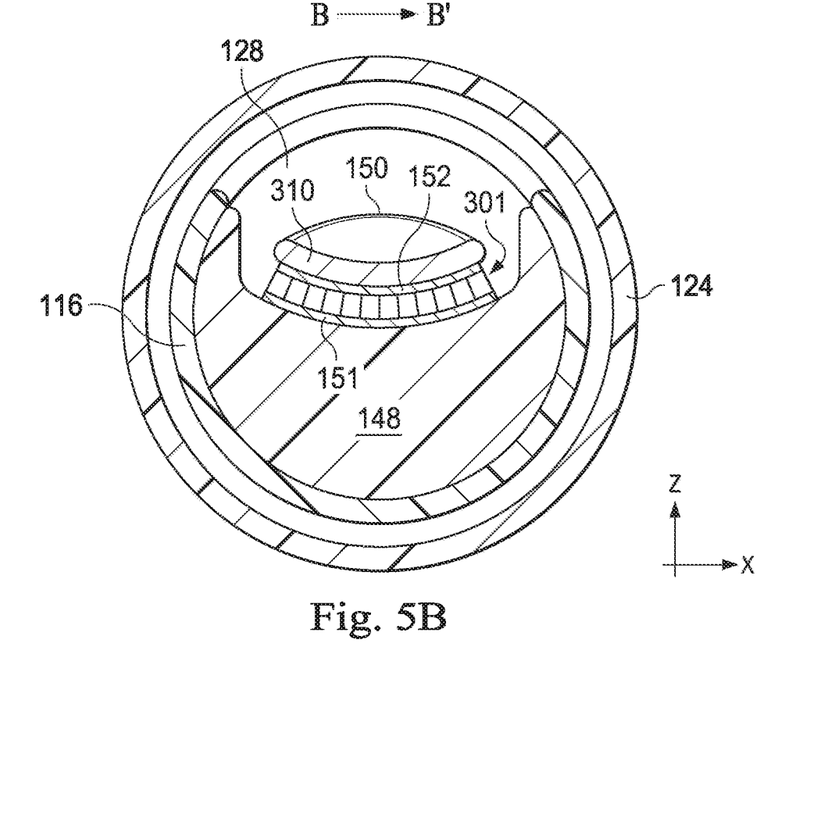
FIG. 5B shows a partial cross-sectional axial view of the distal portion of the imaging device of FIG. 4 along section line B-B'.

FIG. 5B shows a partial cross-section view of transducer housing 116, including ultrasound transducer 150, according to some embodiments. FIG. 5B results from taking a cut away view of FIG. 4 along line BB'. FIG. 5B illustrates aperture 128 in the housing 116 formed above ultrasound transducer 150 to allow ultrasound beam 130 to propagate to and from the vessel tissue. FIG. 5B also shows window 124, which is transparent to the ultrasound beam 130 (cf. FIG. 2).

Figure 6A:
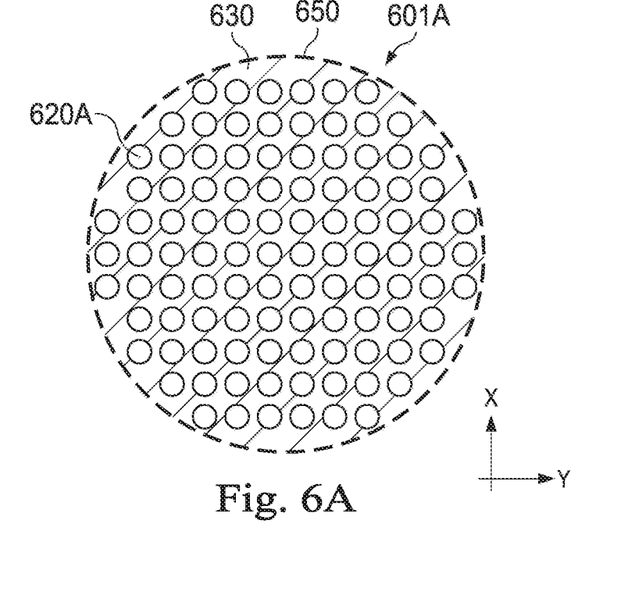
FIG. 6A shows a partial plan view of a single crystal composite according to an embodiment of the present disclosure.
Figure 6B:
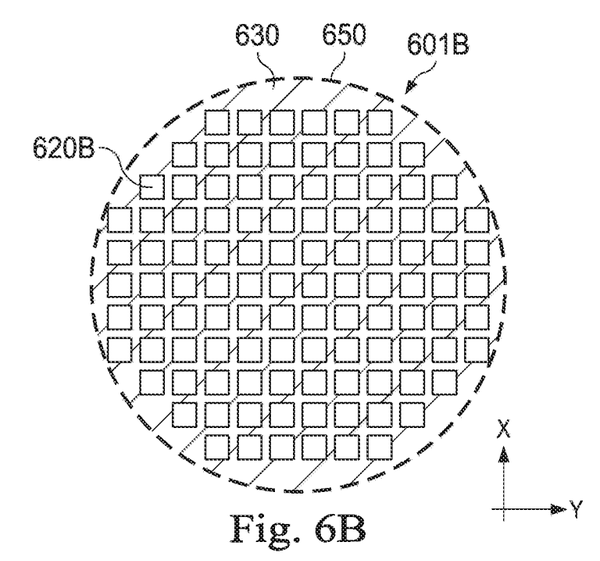
FIG. 6B shows a partial plan view of a single crystal composite according to another embodiment of the present disclosure.
Figure 6C:
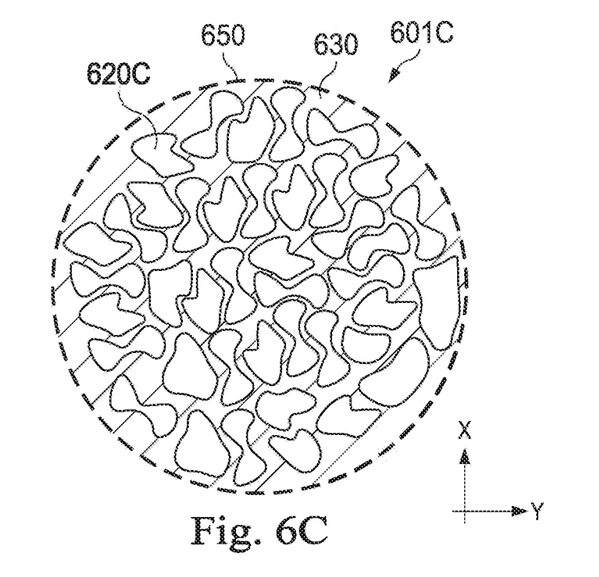
FIG. 6C shows a partial plan view of a single crystal composite according to yet another embodiment of the present disclosure.

FIGS. 6A, 6B, and 6C show partial plan views of single crystal composites 601A, 601B, and 601C, respectively, according to embodiments disclosed herein. Without loss of generality, SCC 601A, SCC 601B, and SCC 601C in FIGS. 6A, 6B, and 6C are shown in a plane XY consistent with Cartesian coordinate axes shown in FIGS. 1-5B. One of ordinary skill in the art will recognize that an ultrasound transducer fabricated from any one of SCC 601A, 601B, and 601C may have any orientation in 3D space. In particular, as has been discussed above, an ultrasound transducer formed from SCC 601A, SCC 601B, and SCC 601C may have a 3D curvature forming a dish shape having a symmetry axis, BD, as shown in FIG. 4. SCC 601A, SCC 601B, and SCC 601C (collectively referred to as SCC 601) include pillars 620A, 620B, and 620C, respectively (collectively referred to as pillars 620). Pillars 620 in SCC 601 are embedded in polymer matrix 630. In some embodiments polymer matrix 630 may be as polymer matrix 330, described in detail with reference to FIG. 3, above. Also illustrated in FIGS. 6A, 6B, and 6C is a cutout path 650 in the XY plane. Cutout path 650 may be formed with a laser beam on portions of SCC 601 including polymer matrix 630. In this regard, the matrix of pillars 620 may be specifically designed to leave cutout path 650 free of obstruction by pillars 620 which might otherwise be more difficult to ablate with the laser as compared to the polymer matrix 630.

As shown in FIG. 6A, SCC 601A includes pillars 620A having a circular cross-section in the XY plane. As shown in FIG. 6B, SCC 601B includes pillars 620B having a square cross-section in the XY plane. As shown in FIG. 6C, SCC 601C includes pillars 620C having puzzle-piece cross-section in the XY plane. One of ordinary skill would recognize that the particular shape of pillars in SCC 601 in the XY plane is not limiting. Some embodiments may include pillars having cross-sections in the XY plane with dog-bone shape, pseudo-random shape, or hexagonal shape.

Embodiments such as SCC 601A, 601B, 601C, or similar non-traditional shapes provide improved fill efficiency in the XY plane, improved adhesion to polymer matrix 630, greater flexibility, and better suppression of undesired lateral modes (in the XY plane). Furthermore, SCC 601 provides improved mechanical integrity during the wafer thinning process. Patterning the finished transducer with cutout path 650 is also a valuable benefit. In some embodiments, cutout path 650 may form a circular or elliptical transducer shape. Ultrasound transducers having circular or elliptical shapes offer good performance in terms of sidelobe levels, compared to cutout paths having rectangular or square shapes.

The geometric configuration of pillars 620 shown in FIG. 6 is not limiting to patterns 620A, 620B, or 620C. One of ordinary skill will recognize that many configurations are possible. In some embodiments the aperture formed by SCC 601 may be apodized by varying the density of pillars 620 near the edges of the aperture (close to cutout path 650) to further reduce sidelobe levels. Some embodiments include pillars 620 having cross-sections chosen to provide regular, semi-regular, or aperiodic tessellation of the substrate in the XY-plane. In some embodiments, odd-shaped but uniform pillars 620 are used.

Figure 7A:
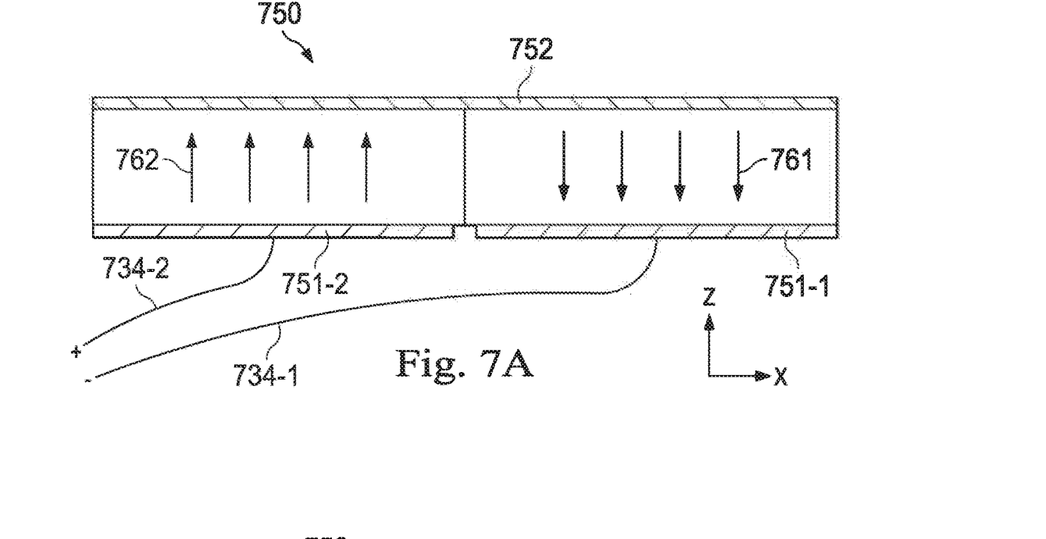
FIG. 7A shows a partial side view of an ultrasound transducer according to an embodiment of the present disclosure.

FIG. 7A shows a partial side view of an ultrasound transducer 750 according to some embodiments disclosed herein. Embodiments of split back electrode transducer 750 include a back electrode divided into two equal electrode halves 751-1 and 751-2. In some embodiments, electrode halves 751-1 and 751-2 have D-shapes where the transducer has a circular or elliptical profile. Electrode halves 751-1 and 751-2 are electrically isolated from one another, while the front electrode is continuous over the entire front surface of transducer 750 in some instances. In ultrasound transducer 750 the electrode connections to electrical cables 734-1 and 734-2 are provided from the back side. Thus, the back electrode in ultrasound transducer 750 includes back side portion 751-1 electrically connected to cable 734-1, and back side portion 751-2 electrically connected to cable 734-2. According to some embodiments, front electrode 752 may be electrically floating with no direct connection to an external potential such as ground, but by way of capacitive coupling through the transducer substrate, front electrode will tend to assume a potential midway between the two potentials present on back electrode halves 751-1 and 751-2. Ultrasound transducer 750 includes SCC 701, which may include pillars embedded in a polymer similar to SCC 301 and SCC 601 as described in detail above (cf. FIGS. 1, 6A, 6B, and 6C).

Some embodiments of ultrasound transducer 750 with a split back electrode configuration as in FIG. 7A include SCC 701 having two halves 701-1 and 701-2, poled in opposite directions but parallel to the Z-axis. For example, a first half SCC 701-1 coupled to electrode 751-1 may be poled in a first direction 761 parallel to the Z-axis, and a second half SCC 701-2 coupled to electrode 751-2 may be poled in a second direction 762 opposite to first direction 761, but parallel to the Z-axis. SCC may support a split polarization without significant artifacts due to the anisotropic electrical properties of the composite arising from the significantly different electrical properties of the piezoelectric crystal material and polymer matrix comprising the composite. According to some embodiments, cable 734-1 may directly couple electrode 751-1 to a first signal, while cable 734-2 may directly couple electrode 751-2 to a second signal of equal magnitude but opposite polarity compared to said first signal. As the two back electrodes are excited with equal magnitude but opposite polarity signals, the front electrode tends to maintain a potential midway between the two signals, which is a neutral or virtual ground potential, and the two transducer halves 701-1 and 701-2 receive equal but opposite polarity electrical excitation. With opposite polarity electrical excitation of the two transducer halves 701-1 and 701-2, combined with their opposite direction poling, both transducer halves 701-1 and 701-2 will expand and contract in phase with one another to provide the same polarity of ultrasound excitation across the entire transducer surface. Accordingly, in some embodiments transducer halves 701-1 and 701-2 vibrate in phase with one another, providing a full aperture ultrasound beam, but without the requirement for an external electrical connection to the front surface of transducer 750 required.

A single crystal composite as disclosed herein is particularly well suited to the split back electrode configuration. Due to the high dielectric constant of the PMN-PT pillars (typical value for relative dielectric constant is 3000) compared to that of the epoxy filler material (typical value for relative dielectric constant is 5), the electric field is largely confined to the high dielectric pillars, and forced to align itself in the Z-direction. Accordingly, the fringe fields at the boundary between the split electrodes 751-1 and 751-2, and between transducer halves 701-1 and 701-2 are minimized and there is very little inefficiency associated with this configuration. This same mechanism constrains the electric field during the poling operation to remain predominantly aligned in the Z-direction, with minimal fringe fields near the boundary between the split electrodes 751-1 and 751-2, and between transducer halves 701-1 and 701-2, thus ensuring that the poling maintains a well-defined orientation parallel to the Z-axis near the boundary between the two halves of the transducer.

Some embodiments using ultrasound transducer 750 including a split electrode may yield a lower capacitance (higher impedance) device. Indeed, each of the two capacitors formed between electrodes 751-1 and 752 or between electrodes 751-2 and 752 has half the area and half the capacitance of the traditional front/back electrode configuration applied of the same SCC 701 substrate. Furthermore, in the split electrode configuration the two capacitors formed between electrodes 751-1 and 752 and between electrodes 751-2 and 752 are connected in series, thus reducing the net capacitance of SCC 701 by another factor of two as compared to the traditional configuration with a single back electrode. Thus, embodiments of SCC 701 having a split back electrode may have a four-fold lower capacitance and four times higher impedance, requiring twice the excitation voltage and half the excitation current to achieve the same ultrasound output as compared to the conventional electrode configuration. Embodiments consistent with the split electrode configuration illustrated in FIG. 7A provide desirable manufacture features, since front electrode 752 is floating and does not require a direct connection to an external voltage source or ground. This simplifies the configuration and manufacturing of ultrasound transducer 750 and tip housing 116 since all of the electrical connections to transducer 750 can be made through features integrated into the housing assembly as the transducer 750 is placed and adhered to the molded backing 148.

Split back electrode transducer 750 is also desirable in embodiments including matching layer 310. The use of a split back electrode permits matching layer 310 to be formed at the wafer level fabrication of transducer 750. For example, an impedance matching layer such as layer 310 (cf. FIG. 3) may be formed as a continuous layer on top of front electrode 752, without the need to interrupt the matching layer to provide access for lead attachment to front electrode 752. Thus, fabrication methods according to some embodiments may avoid cutting a hole in matching layer 310 for a front electrode contact.

Figure 7B:
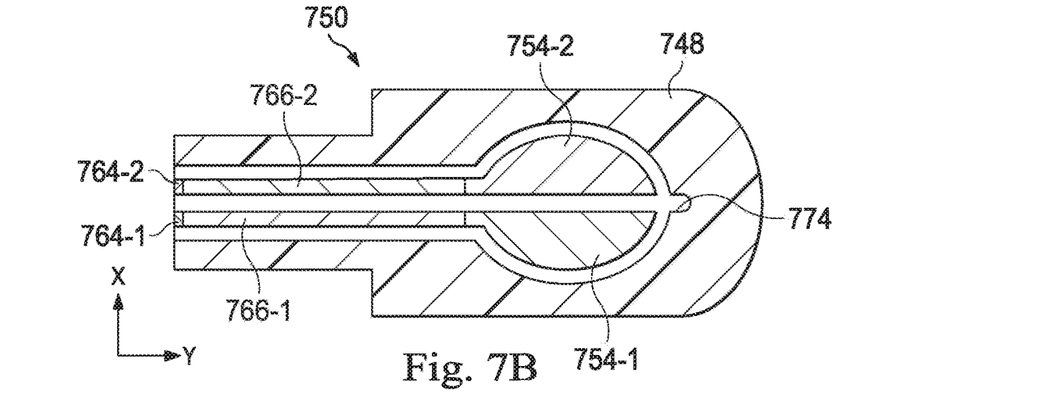
FIG. 7B shows a partial plan view of a distal portion of an imaging device incorporating the ultrasound transducer of FIG. 7A according to an embodiment of the present disclosure.

FIG. 7B shows a partial plan view of molded backing assembly for use with ultrasound transducer 750 according to some embodiments disclosed herein. In some configurations it is preferred to avoid the requirement for direct attachment of leads 134-1 and 134-2 to electrodes 751-1 and 751-2, rather to provide intermediate conductive members integrated into the molded backing 748, to indirectly connect leads 134-1 and 134-2 to electrodes 751-1 and 751-2. FIG. 7B illustrates conductive bonding contacts 754-1 and 754-2 formed on the molded backing 748 in the concave depression where the ultrasound transducer 750 will ultimately be placed and adhered. Bonding contacts 754-1 and 754-2 are connected to lead attachment pads 764-1 and 764-2, also formed on the molded backing 748, respectively, by conductive pathways 766-1 and 766-2, also formed on the molded backing 748. In some embodiments bonding contacts 754-1 and 754-2 may include gold-plated diamond grit to facilitate electrical contact with split back electrodes 751-1 and 751-2 when the ultrasound transducer is placed on and adhered to the molded backing 748. Lead attachment pads 764-1 and 764-2 provide a termination point for electrical cables such as cables 134-1 and 134-2 (cf. FIG.

5A). Lead attachment pads 764-1 and 764-2, conductive pathways 766-1 and 766-2, and bonding contacts 754-1 and 754-2 may be formed of any conductive material, such as gold or silver. One of ordinary skill would recognize that the specific material forming bond pads 761-1 and 761-2 is not limiting and any conductive material or alloy thereof may be used, without limitation.

In embodiments using gold-plated diamond grit, SCC 701 is pressed and glued onto molded backing 748. Thus, protuberances in the diamond grit poke into the electrode plating on the back of the sheet formed by SCC 701, providing a low resistance electrical connection without the need for soldering, welding, conductive adhesive, or other connection method that might be difficult to apply in the confined region between the SCC 701 and molded backing 748. Some embodiments may include anisotropic conductive adhesives to provide a reliable electrical connection to SCC 701 without creating a short circuit between split electrodes 751-1 and 751-2. For example, an insulating epoxy-like material filled with gold- or silver-plated spheres provides an anisotropic conductive adhesive in some implementations. In such embodiments the density of the plated spheres is low enough that the bulk material is nonconductive, but when the adhesive is compressed into a thin film between two conductive surfaces, the plated spheres are compressed between the conductors and they bridge the narrow gap to form a low resistance connection in the compression direction.

Figure 7C:
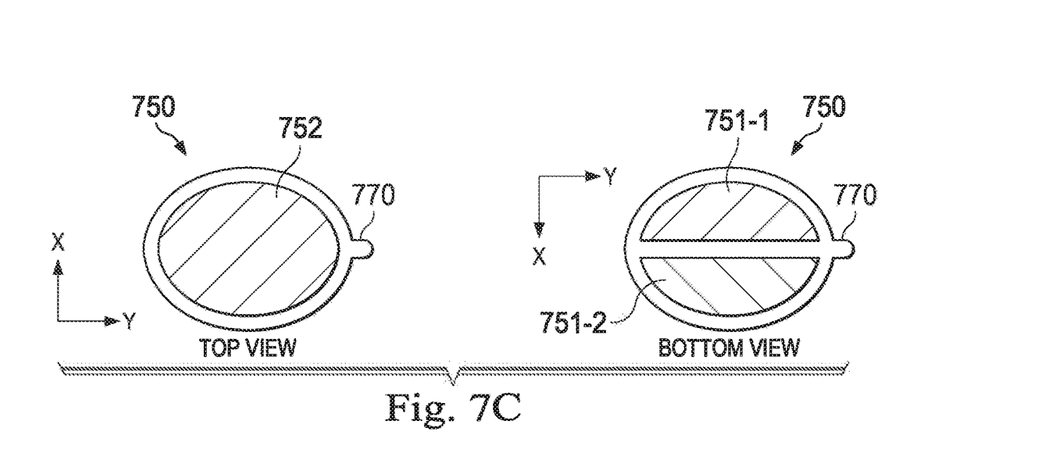
FIG. 7C shows top and bottom plan views of the ultrasound transducer of FIG. 7A according to an embodiment of the present disclosure.

According to some embodiments, transducer 750 including electrodes 752, 751-1, and 751-2 is pressed into molded backing 748 and adhered in place, thus forming a bowl-shaped transducer for providing focused beam 130 (cf. FIG. 4). FIG. 7C shows top and bottom views of transducer 750 according to some embodiments. In some embodiments transducer 750 includes alignment tab 770 which mates with alignment notch 774 within molded backing 748. This alignment feature ensures that the transducer is properly oriented as it is pressed in place and adhered to the molded backing 748.

Figure 8A:
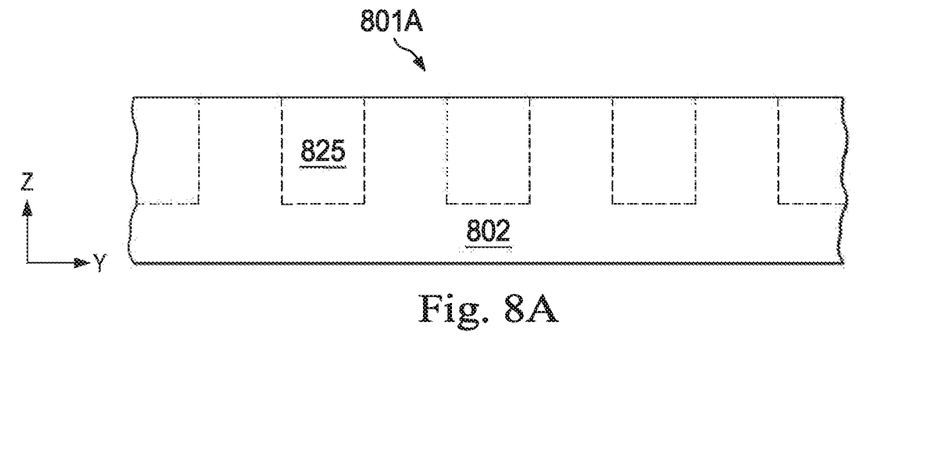
FIGS. 8A-F show a series of partial cross-sectional side views of fabrication stages for an ultrasound transducer according to some embodiments of the present disclosure.

FIGS. 8A-F show a partial view of fabrication stages for a single crystal composite substrate suitable for fabricating ultrasound transducer 150, according to some embodiments. FIG. 8A illustrates a substrate 801A formed from a wafer 802 of single crystal material, patterned using photolithography and DRIE (or other suitable etching/material removal processes) to form a pattern of trenches 825 into the surface of wafer 802, said trenches defining an array of pillars on one surface of the wafer. Wafer 802 may be of any piezoelectric material, although single crystal piezoelectric material is preferred for its superior piezoelectric properties and its suitability for etching using a wider range of wafer processing technologies. For example, some embodiments may use a single crystal of lead magnesium niobate-lead titanate (PMN-PT).

Figure 8B:
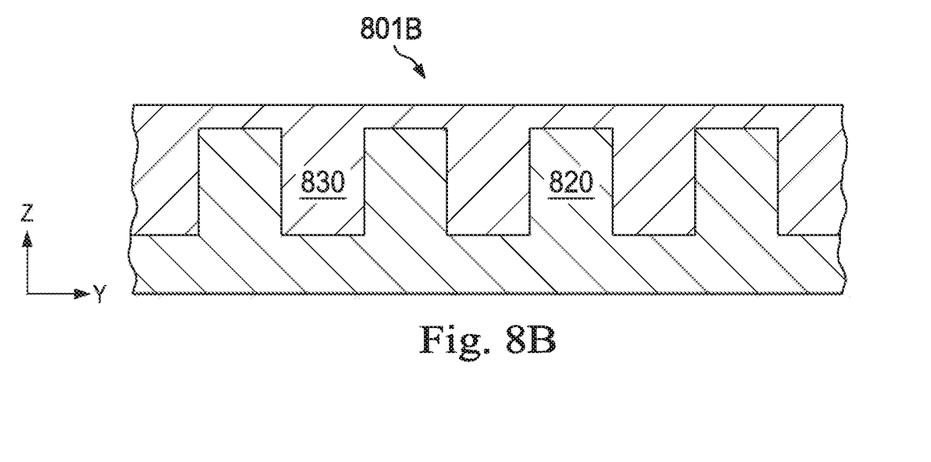

FIG. 8B illustrates filling the trenches of etched wafer 802 with polymer 830 to form substrate 801B. Polymer 830 serves to support pillars 820 of piezoelectric material, and to ultimately provide the polymer matrix 330 of a single crystal composite material. In some embodiments a pattern of trenches is etched in the piezoelectric substrate using DRIE to produce vertical walls (Z-direction) and a precise cross-sectional profile (XY plane), typically with 1 µm resolution. After etching, the trenches are filled with a polymer 830 such as epoxy or silicone, and excess polymer may completely cover pillars 820 to form substrate 801B.

Figure 8C:
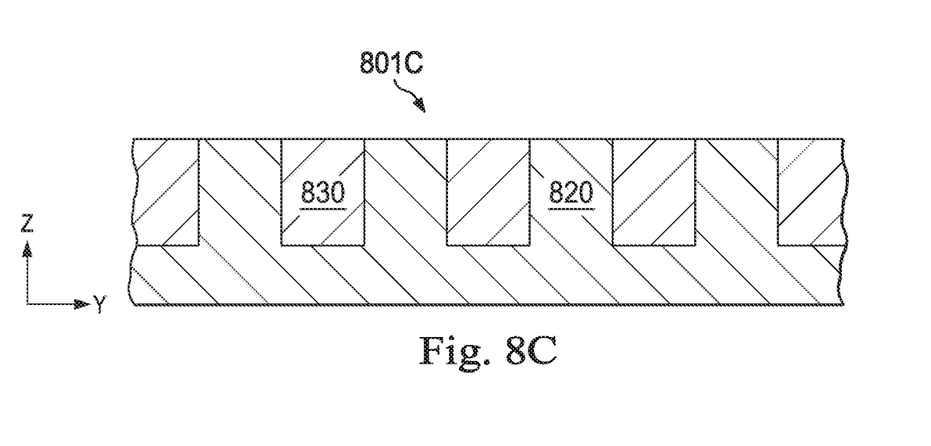

FIG. 8C illustrates the formation of substrate 801C, according to some embodiments. Polymer 830 may completely cover the front surface of substrate 801B. In some embodiments, substrate 801B may be polished, ground, or etched to a thickness such that the top surfaces of pillars 820 are exposed on the surface of substrate 801C, isolated from one another by moats of polymer 830. Preferably, the surface of substrate 801C is flat, with the exposed surfaces of pillars 820 and polymer 830 coplanar with one another.

Figure 8D:
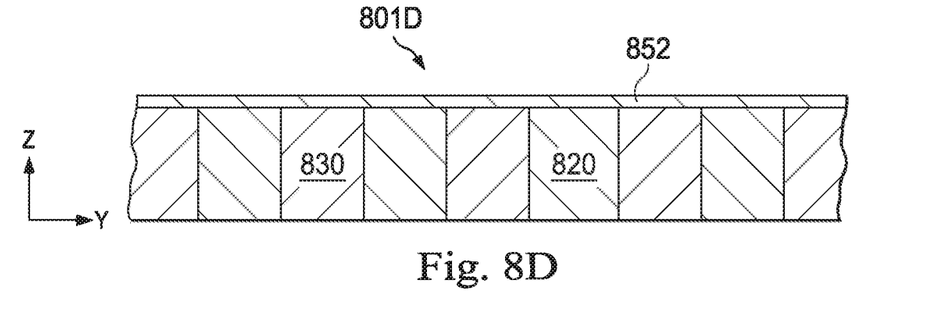

FIG. 8D illustrates forming of substrate 801D, including a front electrode 852. Formation of substrate 801D may include deposition and optional patterning of front electrode 852. In addition to formation of the front electrode 852, substrate 801D is completed by thinning substrate 801C to the desired thickness of single crystal composite material. This thinning operation is accomplished by grinding, polishing, and/or etching the back side of substrate 801C until the desired thickness of substrate 801D is reached. Preferably, the back surface of substrate 801D is flat, with the exposed surfaces of pillars 820 and polymer 830 coplanar with one another. Once substrate 801D is thinned to its final thickness, it becomes a flexible material due to the matrix of flexible polymer 830 supporting the isolated pillars 820. Typically, the electrode is very thin (<1 µm) such that it does not appreciably affect the flexibility of the substrate 801D. Front electrode 852 is formed by deposition on the top surface of substrate 801D of a conductive material by evaporation, sputtering, electroplating, printing, or other method.

Figure 8E:
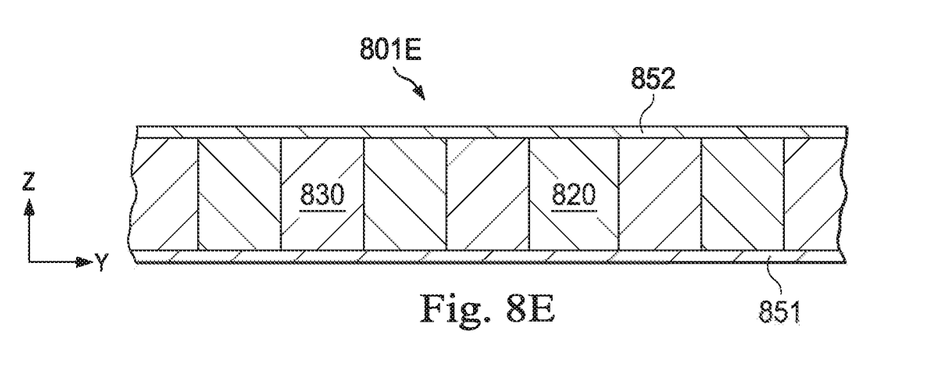

FIG. 8E illustrates the formation of a back electrode 851 on substrate 801E. Back electrode 851 and front electrode 852 may be as electrodes 151 and 152 described in detail above (cf. FIG. 3). Back electrode 851 may be formed by deposition and optional patterning in the same way as front electrode 852 (cf. FIG. 8D).

Figure 8F:
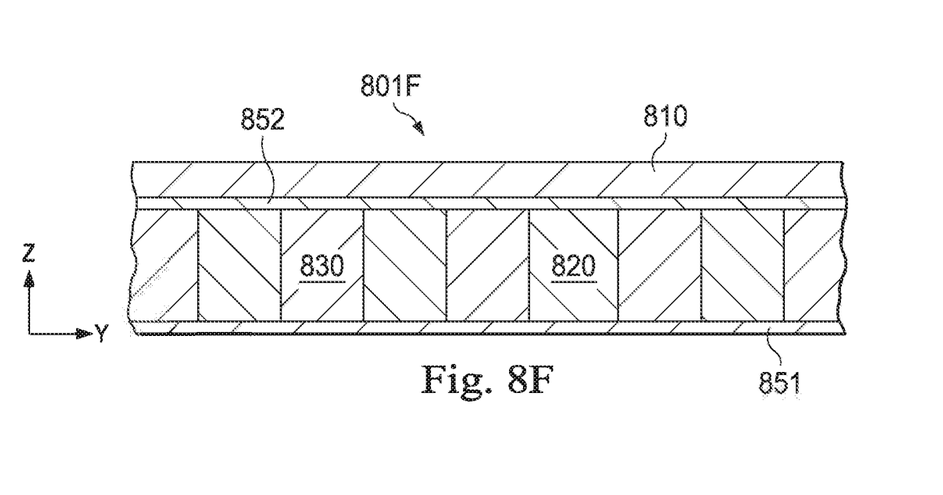

FIG. 8F illustrates a completed substrate of single crystal composite 801 formed by depositing an acoustic impedance matching layer 810 on top of substrate 801E. Acoustic matching layer 810 is included in some embodiments of SCC 801 to better match the acoustic impedance of the vessel tissue. Thus, acoustic matching layer 810 may improve the efficiency or broaden the frequency response of an ultrasound transducer using SCC 801.

One skilled in the art will recognize that the order of fabrication steps outline with respect to FIGS. 8A-F may be altered to optimize the fabrication process, without substantially affecting the finished Once a substrate of SCC 801 is complete as shown in FIG. 8E or FIG. 8F, individual transducer elements can be removed from the sheet of material cutting or removing the polymer matrix in a desired outline around the element. In some embodiments, cutting/removing the polymer matrix surrounding an individual element may be performed using a laser to ablate the material. Once the individual transducer element is removed from the sheet of single crystal composite, it may be mounted to the molded backing 148 inside the transducer housing 116 as ultrasound transducer 150.

According to embodiments of the fabrication method illustrated in FIGS. 8A-F, the dimensions of an ultrasound transducer may be defined at the wafer level. Thus, the dimensions of a finished ultrasound transducer may be determined during the formation of substrate 801A (e.g., photolithography step) and substrate 801B (e.g., DRIE step). The flexibility of DRIE allows the formation of pillars 820 of arbitrary cross-sectional profile, as well as arranging the pillars into any desired configuration so as to define individual transducer elements with particular features such as laser ablation outline free from obstruction, variable pillar density near the edges of the element, etc. In addition, electrodes 851 and 852 may be patterned in alignment to the underlying pillar pattern, such that the individual transducer elements will include the desired electrode pattern (possibly including a split electrode pattern) when removed from the substrate by laser ablation of the transducer outline (or other method).

By providing flexibility in the layout and pattern design of an ultrasound transducer, fabrication methods for SCC layers as disclosed herein provide a focused ultrasound beam using a simple electrical coupling to the transducer.

Figure 9:
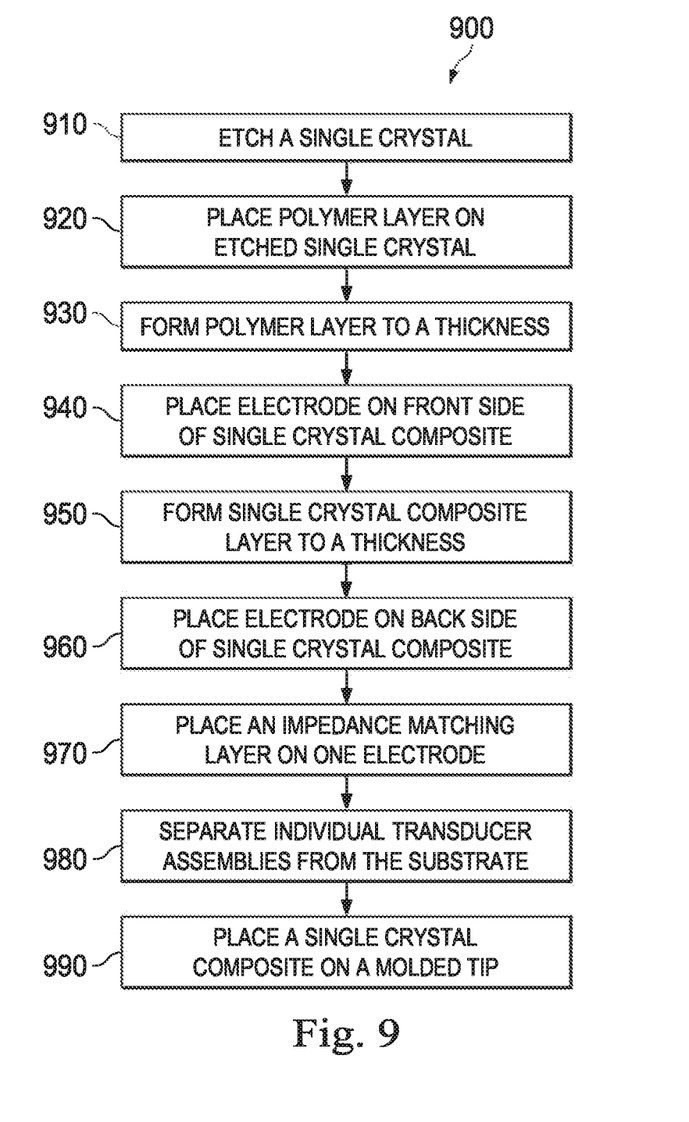
FIG. 9 shows a flow chart for a method of forming an ultrasound transducer according to some embodiments of the present disclosure.

FIG. 9 shows a flow chart for a method 900 of forming an ultrasound transducer according to embodiments disclosed herein. Method 900 will be described below in relation to the steps and structures illustrated in FIGS. 8A-F. Reference to the steps and structures in FIG. 8A-F is used for illustrative purposes only and is not limiting of the embodiments of method 900 consistent with the general concept expressed in FIG. 9. One of ordinary skill would recognize that obvious variations to method 900 may be provided, including changing the order of the steps, while maintaining the overall concept as described below.

Step 910 includes etching a single crystal according to a pattern formed by photolithography, such as in substrate 801A (cf. FIG. 8A). In some embodiments, step 910 includes a DRIE procedure. Step 920 includes placing a polymer layer on the etched single crystal, to form a substrate such as substrate 801B (cf. FIG. 8B). In some embodiments step 920 includes filling a pillar pattern resulting from the etching step 910 with polymer, which may be an epoxy. Step 930 includes forming the polymer layer to a thickness, such as in substrate 801C (cf. FIG. 8C). Step 930 may include lapping the surface of the wafer to removing excess epoxy, creating a planar surface and exposing the pillars. In step 940 an electrode 852 is deposited on the front side of the SCC.

Step 950 includes forming an SCC layer to a thickness, as in substrate 801D (cf. FIG. 8D). In some embodiments step 950 includes grinding and polishing the back portion of the wafer including substrate 801D to release the composite structure from the wafer. Step 960 includes depositing a back electrode 851 to form a substrate such as substrate 801E (cf. FIG. 8E). According to some embodiments, step 960 may include similar procedures as step 940 to deposit an electrode. In some embodiments, substrate 801E is formed to incorporate a pillar structures and electrodes configured to form a plurality of individual transducers on a single substrate.

Step 970 includes placing an impedance matching layer 810 on one electrode. Step 970 may include grinding the matching layer to a desired thickness. Acoustic matching layer may be composed of epoxy (or other polymer), a particle-loaded loaded epoxy composite, graphite, or other material of moderate acoustic impedance chosen according to known methods based on the acoustic impedances of the medium (saline) and the single crystal composite material. Impedance matching layer 810 may be composed of multiple layers in some embodiments. Nominal thickness for a single matching layer or for a single layer of a multi-layer matching structure is one-quarter wavelength in the matching layer material referenced to the center frequency of the transducer. For example, a particle-loaded epoxy composite material may be fabricated to exhibit an acoustic impedance of 5.0 MRayls, and an acoustic velocity of 1.8 mm/μsec, and the corresponding quarter-wave matching layer thickness for a 40 MHz center frequency typical for IVUS imaging would be 11 μm. Matching layer thicknesses and acoustic impedances may be varied from their nominal values to optimize particular aspects of the transducer performance, such as frequency response, bandwidth, etc.

Step 980 may include cutting individual transducers from substrate 801E or 801F. The cutting process could be performed using a laser to remove epoxy filler 830 surrounding isolated groups of pillars 820 that define a single transducer. Thus, the transducer structure can be separated from the substrate by a laser cutting process without damaging the piezoelectric material in pillars 820, or electrodes 851 and 852.

Step 990 includes placing the individual transducer thus formed on a molded backing, such as molded backing 148 or 748. Once the individual transducer is separated from the substrate 801E or 801F, it can be pressed into a micro-molded housing that will become the tip of the flexible driveshaft in a rotational IVUS catheter. The molded housing may include a dish-shaped depression to form the desired aperture deflection. In some embodiments, step 990 is performed once the front and back electrodes are in place (steps 940 and 960). In this respect, molded backing 748 may also include conductive elements to bridge the gap between the electrical leads inside the driveshaft (e.g., a shielded twisted pair) and the split back electrodes of the transducer. Such conductive elements are described in detail above in reference to bonding contacts 754-1 and 754-2 (cf. FIG. 7B). In some embodiments the fabrication process may include a "Cast-In-Can" method to form a transducer on a molded backing. In some embodiments, the transducer is pressed into the micro-molded tip subassembly. In some embodiments the transducer is placed on a molded tip such that acoustic beam 130 is formed in a plane substantially perpendicular to the longitudinal axis of the catheter (XY plane in FIG. 2). According to some embodiments, the transducer is placed on a molded tip such that acoustic beam 130 extends at an oblique angle with respect to the longitudinal axis (Z-axis) of the catheter.

Embodiments of the present disclosure described above are exemplary only. One skilled in the art may recognize various alternative embodiments from those specifically disclosed. Those alternative embodiments are also intended to be within the scope of this disclosure. Accordingly, it is appropriate that the appended claims be construed broadly and in a manner consistent with the present disclosure.

What is claimed is:

1. An IVUS imaging system, comprising:
an ultrasound emitter and receiver rotationally disposed within an elongate member;
an actuator coupled to the ultrasound emitter and receiver, the actuator moving the ultrasound emitter and receiver through at least a portion of an arc; and
a voltage source configured to output a first potential and a second potential;
a control system configured to control emitting of a sequence of pulses and receiving of ultrasound echo data associated with the sequence of pulses by the ultrasound emitter and receiver, the control system processing the ultrasound echo data to generate a cross-sectional image of a vessel,
wherein the ultrasound emitter and receiver comprises a single ultrasound transducer, the single ultrasound transducer comprising:
an electrically floating front electrode; and
a back electrode divided into two equal electrode halves, the back electrode comprising a first electrode half connected to the first potential and a second electrode half connected to the second potential such that the front electrode comprises a third potential, via capacitive coupling, that is between the first potential and the second potential.

2. The IVUS imaging system of claim 1, wherein the single ultrasound transducer further comprises a matching layer based on a center frequency of a pulse transmitted by the single ultrasound transducer.

3. The IVUS imaging system of claim 1, wherein the single ultrasound transducer further comprises a matching layer formed as a continuous layer formed over the front electrode.

4. The IVUS imaging system of claim 1, wherein the first and second electrode halves comprise curved outer edges and straight inner edges, and the front electrode comprises a curved outer edge.

5. The IVUS imaging system of claim 1, wherein the single ultrasound transducer is arranged within the elongate member such that the sequence of pulses propagate at an oblique angle with respect to a longitudinal axis of the elongate member.

6. The IVUS imaging system of claim 1,
wherein the voltage source is configured to output the first potential comprising a first signal having a first polarity and a first magnitude, and the second potential comprising a second signal having a second polarity and a second magnitude,
wherein the first polarity is opposite to the second polarity and the first magnitude is equal to the second magnitude, and
wherein the first electrode half is electrically isolated from the second electrode half.

7. The IVUS imaging system of claim 6, wherein the first electrode half is coupled to a first electrical cable carrying the first signal, the second electrode half is coupled to a second electrical cable carrying the second signal, and the front electrode is without a direct external electrical connection.

8. The IVUS imaging system of claim 7, further comprising intermediate conductive members coupling the first electrical cable to the first electrode half and the second electrical cable to the second electrode half.

9. The IVUS imaging system of claim 1, wherein the single ultrasound transducer comprises a piezoelectric material between the front electrode and the back electrode.

10. The IVUS imaging system of claim 9, wherein the piezoelectric material comprises single crystal composite (SCC) material.

11. The IVUS imaging system of claim 10, wherein the SCC material comprises:
a first SCC half between the front electrode and the first electrode half; and
a second SCC half between the front electrode and the second electrode half.

12. The IVUS imaging system of claim 11, wherein a polarization of the first SCC is in a first direction and the second SCC is in a second direction.

* * * * *